United States Patent
Kragl et al.

(10) Patent No.: US 7,754,462 B2
(45) Date of Patent: Jul. 13, 2010

(54) ENZYME CATALYSIS IN THE PRESENCE OF IONIC LIQUIDS

(75) Inventors: Udo Kragl, Kritzmow (DE); Nicole Kaftzik, Brohl (DE); Sonja Fliege, Langenfeld (DE); Peter Wasserscheid, Cologne (DE)

(73) Assignee: Solvent Innovation GmbH, Cologne (DE)

( * ) Notice: Subject to any disclaimer, the term of this patent is extended or adjusted under 35 U.S.C. 154(b) by 119 days.

(21) Appl. No.: 12/119,214

(22) Filed: May 12, 2008

(65) Prior Publication Data

US 2008/0299623 A1   Dec. 4, 2008

Related U.S. Application Data

(63) Continuation of application No. 11/440,321, filed on May 23, 2006, now abandoned, which is a continuation of application No. 10/416,067, filed as application No. PCT/EP01/12869 on Nov. 7, 2001, now abandoned.

(30) Foreign Application Priority Data

Nov. 8, 2000   (EP) ................. 00124195

(51) Int. Cl.
C12N 9/20 (2006.01)
B01F 1/00 (2006.01)
C07D 233/00 (2006.01)
C07D 213/20 (2006.01)
C07F 9/54 (2006.01)

(52) U.S. Cl. .............. 435/198; 252/364; 548/335.1; 546/347; 568/9

(58) Field of Classification Search .......... 435/198; 252/364; 548/335.1; 546/347; 568/9
See application file for complete search history.

(56) References Cited

U.S. PATENT DOCUMENTS 3,681,197 A   8/1972   Smith

FOREIGN PATENT DOCUMENTS

WO   WO 98/17769   4/1998

OTHER PUBLICATIONS

Proc. Natl. Acad. Sci USA—vol. 92, pp. 7764-7768, Aug. 1995 Biochemistry—"Proenzyme of Manduca Sexta phenol oxidase: Purification, activation, substrate specificity of the active enzyme, and molecular cloning" Martin Hall et al.
Biochem J. (1986) vol. 235, pp. 887-889—"Isolation of streptococcal hyaluronate synthase" Peter Prehm et al.
Experimental data from the Opponent relating to the performance of a cellulast-catalysed hydrolysis of cellulose in a reaction medium comprising an ionic liquid—pp. 1-4.
Chem. Commun., 2001, pp. 425-426—"Enzyme catalysis in ionic liquids: lipase catalysed kinetic resolution of 1-phenylethanol with improved enantioselectivity" Sonja H. Schöfer et al.
Chemtech Sep. 1995—"Nonaqueous ionic liquids as reaction solvents" Yves Chauvin et al., pp. 26-30.
Kinetics and Catalysis, vol. 37, No. 5 1996, pp. 693-697—"Room-Temperature Ionic Liquids: Neoteric Solvents for Clean Catalysts" K.R. Seddon.
J. Chem. Tech. Biotechnol. 1997, vol. 68, 351-356—"Ionic Liquids for Clean Technology" Kenneth R. Seddon.
Science/technology—Mar. 30, 1998, pp. 32-37—"Designer Solvents" Michael Freemantle.
Clean Products and Processes (1999) pp. 223-236—"Ionic Liquids" J.D. Holbrey et al.
Science/technology—May 15, 2000, vol. 78, No. 20, CENEAR 78 20 pp. 37-50 ISSN 0009-2347—"Eyes On Ionic Liquids" Michael Freemantle.
CA 92096, "Enzymatic Reactions in Ionic Liquids", William C. Alston, II and Karno Ng., Department of Chemistry, California State University at San Marcos, San Marcos.
Biotechnol. Prog., 2000, vol. 16., No. 6, M. Erbeldinger et al., 1129-1131.

*Primary Examiner*—Karen Cochrane Carlson
*Assistant Examiner*—Rosanne Kosson
(74) *Attorney, Agent, or Firm*—Millen, White, Zelano & Branigan, P.C.

(57) ABSTRACT

The invention relates to the implementation of enzyme-catalysed reactions in the presence of ionic liquids.

10 Claims, No Drawings

ENZYME CATALYSIS IN THE PRESENCE OF IONIC LIQUIDS

CROSS-REFERENCE TO RELATED APPLICATIONS

This application is a continuation application of U.S. Ser. No. 11/440,321 filed May 23, 2006, now abandoned, which is a continuation application of U.S. Ser. No. 10/416,067 filed Jan. 2, 2004, now abandoned, which is a National Phase entry of International Application No. PCT/EP01/12869 filed Nov. 7, 2001.

The invention relates to compositions comprising an enzyme and ionic liquids as well as a method for carrying out enzyme-catalysed reactions in the presence of ionic liquids.

To date, enzymes have become firmly established as biocatalysts for reactions on the laboratory and industrial scale. Nevertheless, despite all the success with enzymatic reactions, there are still problems such as, for example,

- low productivities as a result of too low educt solubilities;
- low yields in equilibrium reactions;
- insufficient selectivity in regio- and stereoselective conversions;
- product inhibition;
- the occurrence of side reactions (parallel, consecutive reactions).

BACKGROUND OF THE INVENTION

There are known attempts to solve this problem by adding organic solvents (G. Carrea, S. Riva, Angew. Chem. 2000, 112, 2312; J. M. S. Cabral, M. R. Aires-Barros, H. Pinheiro, D. M. P. Prazeres, J. Biotechnol. 1997, 59, 133; M. N. Gupta, Eur. J. Biochem, 1992, 203, 25), by adding salts (A. M. Blinkorsky, Y. L. Khmelnitzky, J. S. Dordick, J. Am. Chem. Soc. 1999, 116, 2697) or by carrying out the reaction in microemulsions (B. Orlich, R. Schomäcker 1999, 65, 357-362). Frequently however, the improvements achieved thereby are not significant and do not justify the additional expenditure, or the enzyme stability decreases severely under these conditions (G. Carrea, S. Riva, Angew. Chem. 2000, 112, 2312). At low temperatures (<100° C.) ionic liquids are melting salts which represent a new class of solvents having a non-molecular ionic character. Although the first representatives have been known since 1914, ionic liquids have only been investigated intensively as solvents for chemical conversions in the last 15 years. Ionic liquids have no measurable vapour pressure. This is a major advantage from the process engineering point of view because in this way, the distillative separation of a reaction mixture is possible as an effective method for product separation. The known problems caused by azeotrope formation between solvents and products do not occur. Ionic liquids are temperature-stable up to above 200° C. By means of a suitable choice of cation and anion, it is possible to gradually adjust the polarity and thereby tune the solubility properties. The range goes from water-miscible ionic liquids through water-immiscible ionic liquids as far as those which themselves form two phases with organic solvents. The skilful utilisation of the extraordinary solubility properties is the key to the successful use of ionic liquids as a new class of solvents.

Ionic liquids have already been successfully used as new types of media in two-phase catalysis or as the medium for liquid-liquid extraction). (P. Wasserscheid, W. Keim, Angew. Chem. 2000, 112, 3926).

According to the invention a substantial increase in the yield and selectivity was surprisingly established during the conversion of a wide range of educts with different enzymes in the presence of ionic liquids, which represents a significant improvement compared with the prior art. No adverse effects of the ionic liquid on the enzyme stability were established and in individual cases, even a stabilising effect was found.

This is unexpected and surprising bearing in mind the ionic nature of the ionic liquids and the strong interactions thereby possible between the ionic liquids and the enzyme with its likewise charged groups.

It was also found that ionic liquids can be used as co-solvents to improve the solubility of educts and products.

SUMMARY OF THE INVENTION

The invention relates to a method for the conversion of substances (educts) in the presence of enzymes as a catalyst in a reaction medium comprising ionic liquids.

The ionic liquid can be miscible with water or immiscible with water. In the same way, it is possible to carry out a single-phase, two-phase or multi-phase reaction.

The ionic liquids comprise compounds having the general formula

where n= 1 or 2 and the anion $[Y]^{n-}$ is selected from the group comprising tetrafluoroborate ($[BF_4]^-$), tetrachloroborate ($[BCl_4]^-$), hexafluorophosphate ($[PF_6]^-$), hexafluoroantimonate ($[SbF_6]^-$), hexafluoroarsenate ($[AsF_6]^-$), tetrachloroaluminate ($[AlCl_4]^-$), trichlorozincate $[(ZnCl_3]^-$), dichlorocuprate, sulphate ($[SO_4]^{2-}$), carbonate ($[CO_3]^{2-}$), fluorosulphonate, [R'—COO]$^-$, [R'—SO$_3$]$^-$ or [(R'—SO$_2$)$_2$N]$^-$, and R' is a linear or branched aliphatic or alicyclic alkyl containing 1 to 12 carbon atoms or a $C_5$-$C_{18}$-aryl, $C_5$-$C_{18}$-aryl-$C_1$-$C_6$-alkyl or $C_1$-$C_6$-alkyl-$C_5$-$C_{18}$-aryl radical that can be substituted by halogen atoms, the cation $[A]^+$ is selected from quaternary ammonium cations having the general formula

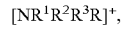

phosphonium cations having the general formula

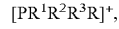

imidazolium cations having the general formula

where the imidizole nucleus can be substituted with at least one group selected from $C_1$-$C_6$-alkyl, $C_1$-$C_6$-alkoxy, $C_1$-$C_6$-aminoalkyl, $C_5$-$C_{12}$-aryl or $C_5$-$C_{12}$-aryl-$C_1$-$C_6$-alkyl groups, pyridinium cations having the general formula

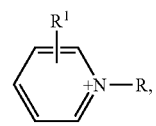

where the pyridine nucleus can be substituted with at least one group selected from $C_1$-$C_6$-alkyl, $C_1$-$C_6$-alkoxy, $C_1$-$C_6$-aminoalkyl, $C_5$-$C_{12}$-aryl or $C_5$-$C_{12}$-aryl-$C_1$-$C_6$-alkyl groups, pyrazolium cations having the general formula

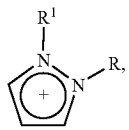

where the pyrazole nucleus can be substituted with at least one group selected from $C_1$-$C_6$-alkyl, $C_1$-$C_6$-alkoxy, $C_1$-$C_6$-aminoalkyl, $C_5$-$C_{12}$-aryl or $C_5$-$C_{12}$-aryl-$C_1$-$C_6$-alkyl groups, and triazolium cations having the general formula

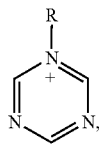

where the triazole nucleus can be substituted with at least one group selected from $C_1$-$C_6$-alkyl, $C_1$-$C_6$-alkoxy, $C_1$-$C_6$-aminoalkyl, $C_5$-$C_{12}$-aryl or $C_5$-$C_{12}$-aryl-$C_1$-$C_6$-alkyl groups, and the radicals $R^1$, $R^2$, $R^3$ are selected independently of one another from the group consisting of hydrogen;

linear or branched, saturated or unsaturated, aliphatic or alicyclic alkyl groups with 1 to 20 carbon atoms;

heteroaryl, heteroaryl-$C_1$-$C_6$-alkyl groups with 3 to 8 carbon atoms in the heteroaryl radical and at least one heteroatom selected from N, O and S which can be substituted with at least one group selected from $C_1$-$C_6$-alkyl groups and/or halogen atoms;

aryl-, aryl-$C_1$-$C_6$-alkyl groups with 5 to 12 carbon atoms in the aryl radical which if necessary can be substituted with at least one $C_1$-$C_6$-alkyl group and/or one halogen atom.

In a further aspect the invention relates to a composition comprising an enzyme and at least one of the ionic liquids defined above. These compositions can be used as the starting point for carrying out the afore-mentioned enzymatically catalysed reactions. Accordingly, in addition to the enzyme (biocatalyst), the compositions according to the invention can also contain the educts (substrate) to be converted and as the reaction proceeds, naturally also the reaction products obtainable by the enzymatic reaction.

A still further aspect is thus the use of ionic liquids, especially the ionic liquids defined above, as the reaction medium or a constituent of the reaction medium in biocatalysis, i.e., carrying out enzymatically catalysed reactions on substrates.

In a particular development of the invention the alkyl, aryl, arylalkyl and alkylaryl sulphonate groups (anion [Y]) can be substituted by halogen atoms, especially fluorine, chlorine or bromine. Especially preferred are the perfluorinated alkyl and afore-mentioned aryl sulphonates such as trifluoromethane sulphonate (triflate). As non-halogenated representatives mention may be made of methane sulphonate, benzene sulphonate and the toluene sulphonate group as well as other sulphonate leaving groups known in the prior art.

In a further development of the invention the alkyl, aryl, arylalkyl and alkylaryl carboxylate groups can be substituted by halogen atoms, especially fluorine, chlorine or bromine. Especially preferred are the fluorinated, in particular the perfluorinated alkyl and above-mentioned aryl carboxylates, such as trifluoromethane carboxylate (trifluoroacetate; $CF_3COO^-$). As non-halogenated representatives mention may be made of the acetate and benzoate group as well as all other carboxylate leaving groups known in the prior art.

In preferred developments of the invention the $C_1$-$C_6$-alkyl groups mentioned in connection with the substituents can be replaced by $C_2$-$C_4$-alkyl groups independently of each other. Likewise, the $C_1$-$C_6$-alkoxy groups mentioned in connection with the substituents can be replaced by $C_2$-$C_4$-alkoxy groups independently of each other. In a further alternative of the invention the $C_5$-$C_{12}$-aryl groups mentioned in connection with the substituents can be replaced by $C_6$-$C_{10}$-aryl groups independently of each other and the $C_3$-$C_8$-heteroaryl groups can be replaced by $C_3$-$C_6$-heteroaryl groups independently of one another. The halogen atoms with which the alkyl, alkoxy and aryl groups can be substituted are selected from fluorine, chlorine, bromine and iodine, preferably fluorine, chlorine and bromine.

In a preferred development the radical R' is a linear or branched aliphatic or alicyclic alkyl containing 1 to 8 carbon atoms or a $C_6$-$C_{10}$-aryl, $C_6$-$C_{10}$-aryl-$C_1$-$C_4$-alkyl or $C_1$-$C_4$-alkyl-$C_6$-$C_{10}$-aryl radical which can be substituted by halogen atoms.

The cations [A] are, for example, selected from trimethylphenyl ammonium, methyltrioctyl ammonium, tetrabutylphosphonium, 3-butyl-1-methyl-imidazolium, 3-ethyl-1-methyl-imidazolium, N-butyl pyridinium, N-ethyl pyridinium, diethyl pyrazolium, 1-ethyl-3-methylimidazolium, 1-butyl-3-methylimidazolium, 1-hexyl-3-methylimidazolium, 1-octyl-3-methylimidazolium, 1-decyl-3-methylimidazolium, 1-butyl-4-methylpyridinium, 1-butyl-3-methylpyridinium, 1-butyl-2-methylpyridinium, 1-butyl-pyridinium, butyl-methyl imidazolium, nonyl-methyl-imidazolium, butyl-methyl-imidazolium, hexyl-methyl-imidazolium, octyl-methyl-imidazolium, 4-methyl-butyl-pyridinium, triethyl ammonium, triethylmethyl ammonium, butylmethyl-pyridinium, propyl ammonium, methyl-methyl-imidazolium, ethyl-methyl-imidazolium, butyl-methyl-imidazolium.

DETAILED DESCRIPTION OF THE INVENTION

Ionic liquids and their production are known in the prior art. For the synthesis of ionic liquids using hexafluorophosphate, tetrafluoroborate, bis(trifluoromethylsulphonyl) amide, perfluoroalkyl sulphonate and perfluoroalkyl carboxylate ions, the corresponding halide salt [cation]$^+$X$^-$ is first formed and isolated by reacting an amine $NR_1R_2R_3$, a phosphane $PR^1R^2R^3$, an imidazole derivative having the general formula $R^1R^{2+}N$=$CR^3$—$R^5$—$R^3C$=$N^+R^1R^2$ or a pyridinium derivative having the general formula $R^1R^2N$=$CR^3R^{4+}$ with an alkyl chloride, alkyl bromide or alkyl iodide (F. H. Hurley, T. P. Wier, Jr., J. Electrochem. Soc. 1951, 98, 207-212; J. S. Wilkes, J. A. Levisky, R. A. Wilson, C. L. Hussey, Inorg. Chem. 1982, 21, 1263-1264; A. A. K. Abdul-Sada, P. W. Ambler, P. K. G. Hodgson, K. R. Seddon, N. J. Steward, WO-A-95/21871) R. H. Dubois, M. J. Zaworotko, P. S. White, Inorg. Chem. 1989, 28, 2019-2020; J. F. Knifton, J. Mol. Catal. 1987, 43, 65-78; C. P. M. Lacroix, F. H. M. Dekker, A. G. Talma, J. W. F. Seetz, EP-A-0989134). Starting from the [A]$^+$X$^-$ halide salt which has been formed and isolated, two different paths are known for the synthesis of ionic liquids using hexafluorophosphate, tetrafluoroborate, bis(trifluoromethyl sulphonyl)-amide, perfluoroalkyl sulphonate and perfluoroalkyl carboxylate ions. On the one hand, the halide salt is converted by the addition of a metal salt MY (with precipitation or separation of the salt MX or the product $[A]^+[Y]^-$ from the respective solvent used) where $[Y]^-$ stands for a hexafluorophosphate, tetrafluoroborate, bis(trifluoromethyl sulphonyl)amide, perfluoroalkyl sulphonate and perfluoroalkyl carboxylate ion and $M^+$ stands for an alkali cation (J. S. Wilkes, M. J. Zaworotko, J. Chem. Soc. Chem. Commun. 1992, 965-967; Y. Chauvin, L. Mußmann, H. Olivier, Angew, Chem. 1995, 107, 2941-2943; P. A. Z. Suarez, J. E. L. Dullius, S. Einloft, R. F. de Souza, J. Dupont, Polyhedron, 1996, 15, 1217-1219; P. Bonhôte, A.-P. Dias, N. Papageorgiou, K. Kalyanasundaram, M. Grätzel, Inorg. Chem. 1996, 35, 1168-1178; C. M. Gordon, J. D. Holbrey, A. R. Kennedy, K. R. Seddon, J. Mater. Chem. 1998, 8, 2627-2638; P. A. Z. Suarez, S. Einloft, J. E. L. Dullius, R. F. de Souza, J. Dupont, J. Chim, Phys. 1998, 95, 1626-1639; A. J. Carmichael, C. Hardacre, J. D. Holbrey, M. Nieuwenhuyzen, K. R. Seddon, Anal. Chem. 1999, 71, 4572-4574; J. D. Holbrey, K. R. Seddon, J. Chem. Soc., Dalton Trans. 1999, 2133-2140). On the other hand, by the addition of a strong acid $H^+[Y]^-$ the halide ion is displaced with the release of $H^+X^-$ and exchanged for $[Y]^-$, where $[Y]^-$ here stands for a hexafluorophosphate, tetrafluoroborate, bis(trifluoromethylsulphonyl)amide, perfluoroalkyl sulphonate and perfluoroalkyl carboxylate ion (J. Fuller, R. T. Carlin, H. C. de Long, D. Haworth, J. Chem. Soc. Chem. Commun, 1994, 299-300), However, ionic liquids can especially advantageously be produced halide-free using the method described in EP 00118441.5.

In a development of the method according to the invention the ionic liquid is used as the only reaction medium, i.e., free from further solvents. The fraction of the ionic liquid in the reaction medium can however be between 0.1 and 99.9 percent by volume, preferably between 5 and 75 percent by volume, more preferably between 15 or 50 and 75 percent by volume relative to the total quantity of the reaction medium.

In addition to the ionic liquid, the reaction medium can also contain a further solvent. This can be selected from the group consisting of water, buffer solutions (pH 2 to 10, preferably 5 to 8) and organic solvents. Usable organic solvents are miscible with water or immiscible with water. As examples of organic solvents mention may be made of methyl-tert-butyl ether, toluene, hexane, heptane, tert-butanol, glycols, polyalkylene glycols. In addition, however, fundamentally all conventional solvents known in the field of enzyme catalysis can be considered.

All enzymes in EC classes 1 to 6 can fundamentally be considered. The enzyme classification is recommended by the "Nomenclature Committee of the International Union of Biochemistry and Molecular Biology" (IUBMB). The enzyme is either homogeneously dissolved but can also be used as a suspension or as an immobilisate on an inert carrier.

It was found according to the invention that the presence of ionic liquids in the reaction medium during enzymatically catalysed reactions results in an improvement in the substrate solubility (biocompatibility), an improvement in the enzyme activity, an improvement in the selectivity, a reduction in product inhibition, suppression of side reactions (parallel, consecutive reactions) and/or an increase in enzyme stability. The examples prove that enzymes from different classes can be used, wherein the use of ionic liquids offers significant advantages, such as, for example, an increase in the activity in the case of formate dehydrogenase, a significant increase in the yield in reactions with galactosidase, an increase in the enantioselectivity for lipases and an improvement in the educt solubility for hydrophobic educts.

According to the invention, the enzyme together with the total quantity of ionic liquid or a part thereof can be used repeatedly or in continuously operated reactors.

The enzymes can be selected from the class of oxidoreductases for regio- and stereoselective oxidation and reduction, from the class of glycosidases for the synthesis of oligosaccharides, from the class of lipases to obtain optically active products (among others, alcohols, amines, carboxylic acids) and from the class of lyases for synthesis, and hydrolases.

The method according to the invention can be carried out at temperatures between $-10°$ C. and $130°$ C., preferably in a temperature range between $10°$ C. and $80°$ C., especially preferably in a temperature range between $20°$ C. and $40°$ C.

The method can be carried out in a single-phase fashion or in a multiphase reaction system.

Some effects arising from the use of ionic liquids as a reaction medium or as a constituent of reaction media for enzymatic reactions will be described below as examples. For example, alcohol dehydrogenases from various sources are used among others for the enzymatic reduction of ketones. The solubility of hydrophobic ketones can be improved by the addition of organic solvents; however, this generally results in a reduction in the enzyme activity and stability (W. Hummel, Biochem. Eng. Biotechnol. 1997, 58, 145; A. Liese, T. Zelinski, M.-R. Kula, H. Kierkels, M. Karutz, U. Kragl, C. Wandrey, J. Mol. Cat. B 1998, 4, 91). In a similar fashion, water-miscible ionic liquids can be added to the reaction medium to increase the educt solubility. For the formate dehydrogenase used for cofactor regeneration, an increase in the reaction rate compared with the purely aqueous system is observed in the same concentration range of the ionic liquid (see Example 1). No deactivation of the enzyme was observed even when the time of influence of the ionic liquid was fairly long. Thus, ionic liquids offer a valuable possibility for increasing the productivity of enzymatic reactions through an increase in the educt concentration. This is especially interesting for barely soluble to very barely soluble educts such as aromatic ketones or steroids.

For about 20 years glycosidases have not only been used for breaking bonds between saccharides but also for the synthesis of di- and oligosaccharides. Despite many attempts to use water-miscible solvents (leads to reduced enzyme stability), by means of the generally expensive activation of educts, yields no greater than 31% have been obtained even in the most recent studies (J. H. Yoon, J. S. Rhee, Carbohydr. Res. 2000, 327, 377; M. J. Hernaiz, D. H. G. Crout, J. Mol. Cat. B 2000, 10, 403). The main problem in these reactions is the immediately initiated secondary hydrolysis of the product, catalysed by the same enzyme. Surprisingly, this secondary hydrolysis is almost completely suppressed in the presence of ionic liquids with otherwise the same enzyme activity. For the example of β-galactosidase-catalysed synthesis of N-acetyl lactosamine, an important building block for pharmacologically relevant oligosaccharide, it was shown that the presence of ionic liquids increases the yield above 55% when using lactose as an inexpensive donor. A maximum of 30% is achieved without the addition of ionic liquids; however, the product concentration drops rapidly to values of <10% as a result of the secondary hydrolysis. Since the secondary hydrolysis does not take place in the presence of ionic liquids, a simplified reaction process is obtained since it is not necessary to follow the reaction and interrupt it at the maximum product yield. The galactosidase is very stable in the presence of ionic liquids and can be repeatedly used after separation by means of ultrafiltration without any change in the attainable yield and the product formation rate.

Ionic liquids also offer advantages in reverse hydrolysis for the synthesis of di- and oligosaccharides. In this case, high educt concentrations together with additives, usually organic solvents, are used to reduce the water activity. Here ionic liquids especially offer the advantage of a very good dissolving capacity for carbohydrates. In the enzymatic synthesis of lactose, it was possible to increase the yield by a factor of 2 and reduce the reaction time by a factor of 5 compared with the literature (K. Ajisaka, H. Fujimoto, H. Nishida, Carbohydr. Res. 180, 35-42 (1988)).

The use of lipases in the presence of organic solvents in single- or two-phase reactions is prior art (G. Carrea, S. Riva, Angew. Chem., 2000, 112, 2312, U. T. Bornscheuer, R. J. Kazlauskas, Hydrolases in Organic Synthesis—Regio- and stereoselective Biotransformations, Wiley-VCH, Weinheim, 1999; A. Liese, K. Seelbach, C. Wandrey, Industrial Biotransformations, Wiley-VCH, Weinheim, 2000; M. C. Parker, S. A. Brown, L. Robertson, N. J. Turner, Chem. Commun. 1998, 2247). However, the enzyme has so far conventionally been separated by filtration and the reaction solution conventionally separated by distillation and the solvent fed back. The use of ionic liquids permits direct distillative separation of the reactands from the reaction mixture even in the presence of the enzyme so that a simplified procedure results. If the reactands possess suitable volatility, this procedure is not limited to lipases. In an investigation of various lipases for racemate splitting in the presence of ionic liquids it was surprisingly established in several cases that the conversion rate and the enantioselectivity are in some cases significantly improved, in individual cases a factor of 5 better. The reaction in tert-butylmethyl ether which is also used as a solvent for lipase-catalysed reactions in industrial processes, is used for comparison.

The results show that ionic liquids as a reaction medium for enzymatic conversions have numerous advantages compared with the conditions established as the prior art and can be used as biocompatible solvents to specifically influence conversions.

The invention is described in detail by the following examples without however being restricted to these.

EXAMPLES

The following abbreviations were used for the description of components used in the examples:

| | | |
|---|---|---|
| tert-butylmethylether | tBME, | MTBE |
| Butyl-methyl-imidazolium $PF_6^-$ | $BMIm^+$ | $PF_6^-$ |
| Nonyl-methyl-imidazolium $PF_6^-$ | $NMIm^+$ | $PF_6^-$ |
| Butyl-methyl-imidazolium $BF_4^-$ | $BMIm^+$ | $BF_4^-$ |
| Hexyl-methyl-imidazolium $BF_4^-$ | $HMIm^+$ | $BF_4^-$ |
| Octyl-methyl-imidazolium $BF_4^-$ | $OMIm^+$ | $BF_4^-$ |
| 4-methyl-butyl-pyridinium $BF_4^-$ | $4\text{-}MBPy^+$ | $BF_4^-$ |
| Triethylammonium-methyl sulphate | $Et_3NH^+$ | $MeSO_4^-$ |
| Triethylmethylammonium-methyl sulphate | $Et_3NMe^+$ | $MeSO_4^-$ |
| Butylmethyl-pyridinium $BF_4^-$ | $BMPy^+$ | $BF_4^-$ |
| Propylammonium-nitrate | $PrNH_3^+$ | $NO_3^-$ |
| Methyl-methyl-imidazolium-methyl sulphate | $MMIm^+$ | $MeSO_4^-$ |
| Ethyl-methyl-imidazolium-benzoate | $EMIm^+$ | $PhCO_2^-$ |
| Butyl-methyl-imidazolium-trifluoro methane sulphonate (=triflate) | $BMIm^+$ | $CF_3SO_3^-$ |
| Butyl-methyl-imidazolium-bis-trifluoromethyl | $BMIm^+$ | $(CF_3SO_2)_2N^-$ sulphonyl)-imidate |

1. Formate Dehydrogenase from *Candida boidinii* (FDH)

The FDH-catalysed oxidation of formic acid to carbon dioxide by the reduction of nicotinamide adenine dinucleotide ($NAD^+$ to $NADH+H^+$) is used as the test reaction to determine the enzyme activity. In the enzyme assay the increase in NADH with time at 25° C. is detected photometrically at a wavelength of 340 nm.

Composition of the enzyme assay: 1 ml buffer solution (50 mM triethanolamine hydrochloride, 1 mM dithiothreitol, hydrochloric acid) pH 7 is mixed with 0.1 ml of aqueous sodium formate solution (2.4 M) and 0.1 ml of enzyme solution (0.7 mg/ml, 8.4 U). The enzyme solution already contains the cofactor NAD (6 mM).

In order to test the influence of water-soluble ionic liquids on the enzyme activity, the volume of the buffer solution in the assay is gradually reduced by 25 vol % and replaced by the ionic liquid.

TABLE 1

NAD reduction by formate dehydrogenase from *Candida boidinii*; enzyme activity compared with the standard reaction in the buffer solution (+) good to better, (±) the same.

| Ionic liquid | 25 vol % | 50 vol % | 75 vol % |
|---|---|---|---|
| $MMIm^+\ MeSO_4^-$ | ± | + | + |

2. β-Galactosidase from *Bacillus circulans* for Synthesis of N-Acetyl Lactosamine The influence of ionic liquids on the progress of β-Gal-catalysed transgalactosylation starting from lactose and N-acetyl glucosamine is studied. For this purpose concentration-time profiles of this synthesis in the presence and absence of ionic liquids are recorded and compared.

In each series of tests 10 reactions were started in parallel in 1 ml GC glasses. At 10 minute intervals the reactions are stopped by boiling at 100° C., the reaction solution is filtered (Minisart RC 4 Sartorius injection filter) and the concentration of the reaction components at this time is determined chromatographically (Aminex HPX-87H cation exchange column from BioRad with a corresponding pre-column, 0.006 M sulphuric acid as eluent with a flux of 0.8 ml/min and a column temperature of 65° C. Detection is accomplished using UV at 208 nm and using the refractive index).

Composition of the reaction mixture: 0.05 ml buffer solution (65 mM $KH_2PO_4$, 195 mM $K_2HPO_4$) pH 7.3 is mixed with 0.5 ml N-acetyl glucosamine solution (GlcNAc 600 mM or 1.2 M in buffer solution), 0.25 ml lactose solution (250 mM in buffer solution) and 0.2 ml enzyme solution (10 mg/ml in buffer solution).

By exchanging buffer solution for ionic liquid in the substrate solutions, the fraction of ionic liquid in the reaction medium is gradually increased. The following substrate solutions are thus obtained:

TABLE 2

Synthesis of N-acetyl lactosamine by β- galactosidase from *Bacillus circulans* with and without ionic liquid

| Reaction medium | Fraction [vol %] | Lactose/ GlcNAc ratio | Yield [%] after 60 min | Yield [%] after 100 min |
|---|---|---|---|---|
| Phosphate buffer | | 1:2.4 | 5 | 3 |

TABLE 2-continued

Synthesis of N-acetyl lactosamine by β- galactosidase from *Bacillus circulans* with and without ionic liquid

| Reaction medium | Fraction [vol %] | Lactose/ GlcNAc ratio | Yield [%] after 60 min | Yield [%] after 100 min |
|---|---|---|---|---|
| MMIm⁺ MeSO₄⁻ | a) 12.5 | 1:2.4 | 40 | 40 |
| | b) 18.75 | 1:2.4 | 44 | 43 |
| | c) 25 | 1:4.8 | 49 | 55 (90 min) |
| BMIm⁺ H₂PO₄⁻/Cl⁻ | d) 12.5 | 1:2.4 | 39 | 30 | a) 0.50 ml N-acetyl glucosamine solution (600 mM in 1:4 MMIm⁺ MeSO₄⁻:buffer solution)
b) 0.50 ml N-acetyl glucosamine solution (600 mM in 1:4 MMIm⁺ MeSO₄⁻:buffer solution) 0.25 ml lactose solution (250 mM in 1:4 MMIm⁺ MeSO₄⁻:buffer solution)
c) 0.50 ml N-acetyl glucosamine solution (1.2 M in 1:2 MMIm⁺ MeSO₄⁻:buffer solution) 0.25 ml lactose solution (250 mM in 1:2 MMIm⁺ MeSO₄⁻:buffer solution)
d) 0.50 ml N-acetyl glucosamine solution (600 mM in 1:4 BMIm⁺ H₂PO₄⁻/Cl⁻:buffer solution)

3. Enantioselective Acylation of R, S-1-phenylethanol by Catalysis with Lipase from *Candida antarctica* (Type B) in Ionic Liquids 4.4 ml of an ionic liquid in accordance with Table 3 or tert-butylmethyl ether are mixed with 122 µl of vinyl acetate and 54 µl of 1-phenyl ethanol so that a substrate solution with approximately 0.1 mol/l of 1-phenyl ethanol and 0.3 mol/l of vinyl acetate is obtained. Each 1 mg of lyophilised lipase (>120 U/mg) is mixed with 0.4 ml of substrate solution, thoroughly mixed and incubated at 24° C. for 3-4 days, shaking slightly.

For further processing 100 µl of the reaction formulation is mixed with 1 ml of n-hexane/Isopropanol (97.5/2.5 v/v) and mixed thoroughly. This hexane/isopropanol extract is used to determine the concentrations and enantiomer ratios of 1-phenyl ethanol and 1-phenylethyl acetate using HPLC. The conversion and the enantiomer excess were calculated from these concentrations (see Table 3).

HPLC Conditions:

TABLE 3

Enantioselective acylation of 1-phenyl ethanol, catalysed by lipase from *Candida antarctica* (Type B): conversion and enantiomer excess in ionic liquids compared to the standard reaction in tert-butylmethyl ether; (+) good to better, (±) the same, (−) poor to none.

| Column: | Guard column Nucleosil C-18 5 µm; 10 mm, 4.6 mm ID; Preparatory column Chiracel OJ; 50 mm, 4.6 mm ID; Separating column Chiracel OJ; 250 mm, 4.6 mm ID |
|---|---|
| Eluent: | isocratic; 96.5% (v/v) n-hexane, 3.0% (v/v) isopropanol, 0.5% (v/v) ethanol |
| Flux rate: | 1 ml/min |
| Temperature: | 38° C. |
| Detection: | UV detector (205 nm) |

| Ionic liquid/solvent | Conversion | Enantiomer excess |
|---|---|---|
| NMIm⁺ PF₆⁻ | ± | + |
| BMIm⁺ BF₄⁻ | + | + |
| HMIm⁺ BF₄⁻ | ± | + |
| OMIm⁺ BF₄⁻ | + | + |
| 4-MBP⁺ BF₄⁻ | + | + |
| BMIm⁺ CF₃SO₃⁻ | + | + |
| BMIm⁺ (CF₃SO₂)₂N⁻ | + | + |

4. Enantioselective Acylation of R,S-1-phenyl Ethanol by Catalysis with Lipase from *Candida antarctica* (Type A) in Ionic Liquids Each 5 mg of lyophilised lipase (>30 U/mg) is mixed with 0.4 ml of a substrate solution as in Example 3. The further procedure corresponds to that described in Example 3.

TABLE 4

Enantioselective acylation of 1-phenyl ethanol, catalysed by lipase from *Candida antarctica* (Type A): conversion and enantiomer excess in ionic liquids compared to the standard reaction in tert-butylmethyl ether; (+) good to better, (±) the same, (−) poor to none.

| Ionic liquid/solvent | Conversion | Enantiomer excess |
|---|---|---|
| BMIm⁺ PF₆⁻ | + | + |
| NMIm⁺ PF₆⁻ | + | + |
| BMIm⁺ BF₄⁻ | ± | + |
| HMIm⁺ BF₄⁻ | + | + |
| OMIm⁺ BF₄⁻ | + | ± |
| BMIm⁺ CF₃SO₃⁻ | + | + |

5. Enantioselective Acylation of R,S-1-phenyl Ethanol by Catalysis of Lipase from *Pseudomonas* sp. in Ionic Liquids Each 3 mg of lyophilised lipase (400 U/mg) is mixed with 0.4 ml of a substrate solution as in Example 3. The further procedure corresponds to that described in Example 3.

TABLE 5

Enantioselective acylation of 1-phenyl ethanol, catalysed by lipase from *Pseudomonas* sp.: conversion and enantiomer excess in ionic liquids compared to the standard reaction in tert-butylmethyl ether; (+) good to better, (±) the same, (−) poor to none.

| Ionic liquid/solvent | Conversion | Enantiomer excess |
|---|---|---|
| MIm⁺ PF₆⁻ | ± | + |
| 4-MBP⁺ BF₄⁻ | ± | + |
| BMIm⁺ CF₃SO₃⁻ | + | + |
| BMIm⁺ (CF₃SO₂)₂N⁻ | + | + |

6. Enantioselective Acylation of R,S-1-phenyl Ethanol by Catalysis of Lipase from *Alcaligines* sp. in Ionic Solvents Bach 5 mg of lyophilised lipase (>20 U/mg) is mixed with 0.4 ml of a substrate solution as in Example 3. The further procedure corresponds to that described in Example 3.

TABLE 6

Enantioselective acylation of 1-phenyl ethanol, catalysed by lipase from *Alcaligines* sp.: conversion and enantiomer excess in ionic liquids compared to the standard reaction in tert-butylmethyl ether; (+) good to better, (±) the same, (−) poor to none.

| Ionic liquid/solvent | Conversion | Enantiomer excess |
|---|---|---|
| BMIm⁺ PF₆⁻ | ± | + |
| BMIm⁺ BF₄⁻ | ± | + |
| HMIm⁺ BF₄⁻ | ± | + |
| OMIm⁺ BF₄⁻ | ± | + |
| 4-MBP⁺ BF₄⁻ | ± | + |
| BMIm⁺ CF₃SO₃⁻ | ± | + |

7. Recycling of the Lipase from *Candida antarctica* (Type B) in Ionic Liquids by Distillation 600 mg of lyophilised lipase (approx. 10 U/mg) is mixed with 4 ml of ionic liquid (BMIm⁺(CF₃SO₂)₂N⁻), 1.2 ml of vinyl acetate and 0.7 ml 1-phenyl ethanol and thoroughly mixed. The reaction mixture is incubated for 40 min at 40° C.

The non-converted educts and the reaction product 1-phenyl acetate is then distilled off (85° C., 0.06 mbar).

The enzyme/ionic liquid mixture is cooled, re-mixed with 1.2 ml of vinyl acetate and 0.7 ml of 1-phenyl ethanol and again incubated for 40 min at 40° C.

The reaction sequence involving incubation and distilling off can be repeated many times without the lipase activity diminishing.

8. Synthesis of Lactose by Reverse Hydrolysis with β-Galactosidase from *Bacillus circulans*

100 mmol/l of glucose, 20 mmol/l of galactose and 2 mg/ml of galactosidase are incubated at 35° C. in a mixture of water and MMIm MeSO$_4$ for 24 h. The reaction is stopped by boiling for 10 minutes at 100° C., the reaction solution is filtered (Minisart RC 4 Sartorius injection filter) and the concentration of the reaction components at this time is determined chromatographically (Aminex HPX-87H cation exchange column from BioRad with corresponding preparatory column, 0.006 M sulphuric acid as eluent with a flux of 0.8 ml/min and a column temperature of 65° C. Detection is accomplished using UV at 208 nm and using the refractive index).

The fraction of ionic liquid is increased from 0 to 100 percent by volume. As a result of water traces in the ionic liquid and the educts, a water content of 0.6% is obtained for 100% ionic liquid. After 24 hours, the conversion no longer increases. The following lactose yields are obtained depending on the quantity of ionic liquid:

| Fraction of ionic liquid in % | Yield [%] |
|---|---|
| 0 | 0 |
| 10 | 0 |
| 20 | 0 |
| 30 | 4 |
| 40 | 12 |
| 50 | 15 |
| 60 | 15 |
| 70 | 16 |
| 80 | 16 |
| 90 | 16 |
| 100 | 17 |

The invention claimed is:

1. A method for the conversion of substances in the presence of a lipase as a catalyst in a reaction medium comprising at least one ionic liquid and one substance, wherein the substance is a substrate for the lipase, comprising the step of contacting the substance with the lipase to convert the substance to a product.

2. The method according to claim 1, characterised in that the ionic liquid has the general formula

[A]$_n^+$[Y]$^{n-}$, where n=1 or 2 and the anion [Y]$^{n-}$ is selected from the group comprising tetrafluoroborate ([BF$_4$]$^-$), tetrachloroborate ([BCl$_4$]$^-$), hexafluorophosphate ([PF$_6$]$^-$), hexafluoroantimonate ([SbF$_6$]$^-$), hexafluoroarsenate ([AsF$_6$]$^-$), tetrachloroaluminate ([AlCl$_4$]$^-$), trichlorozincate ([ZnCl$_3$]$^-$), dichlorocuprate, sulphate ([SO$_4$]$^{2-}$), carbonate ([CO$_3$]$^{2-}$), fluorosulphonate, [R'—COO]$^-$, [R'—SO$_3$]$^-$ or [(R'—SO$_2$)$_2$N]$^-$, and R' is a linear or branched aliphatic or alicyclic alkyl containing 1 to 12 carbon atoms or a C$_5$-C$_{18}$-aryl, C$_5$-C$_{18}$-aryl-C$_1$-C$_6$-alkyl or C$_1$-C$_6$-alkyl-C$_5$-C$_{18}$-aryl radical that can be substituted by halogen atoms, the cation [A]$^+$ is selected from quaternary ammonium cations having the general formula

[NR$^1$R$^2$R$^3$R]$^+$, phosphonium cations having the general formula

[PR$^1$R$^2$R$^3$R]$^+$, imidazolium cations having the general formula

where the imidizole nucleus can be substituted with at least one group selected from C$_1$-C$_6$-alkyl, C$_1$-C$_6$-alkoxy, C$_1$-C$_6$-aminoalkyl, C$_5$-C$_{12}$-aryl or C$_5$-C$_{12}$-aryl-C$_1$-C$_6$-alkyl groups, pyridinium cations having the general formula

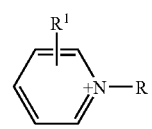

where the pyridine nucleus can be substituted with at least one group selected from C$_1$-C$_6$-alkyl, C$_1$-C$_6$-alkoxy, C$_1$-C$_6$-aminoalkyl, C$_5$-C$_{12}$-aryl or C$_5$-C$_{12}$-aryl-C$_1$-C$_6$-alkyl groups, pyrazolium cations having the general formula

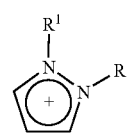

where the pyrazole nucleus can be substituted with at least one group selected from C$_1$-C$_6$-alkyl, C$_1$-C$_6$-alkoxy, C$_1$-C$_6$-aminoalkyl, C$_5$-C$_{12}$-aryl or C$_5$-C$_{12}$-aryl-C$_1$-C$_6$-alkyl groups, and triazolium cations having the general formula

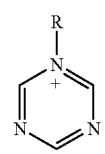

where the triazole nucleus can be substituted with at least one group selected from C$_1$-C$_6$-alkyl, C$_1$-C$_6$-alkoxy, C$_1$-C$_6$-aminoalkyl, C$_5$-C$_{12}$-aryl or C$_5$-C$_{12}$-aryl-C$_1$-C$_6$-alkyl groups, and the radicals R$^1$, R$^2$, R$^3$ are selected independently of one another from the group consisting of hydrogen;

linear or branched, saturated or unsaturated, aliphatic or alicyclic alkyl groups with 1 to 20 carbon atoms;

heteroaryl, heteroaryl-$C_1$-$C_6$-alkyl groups with 3 to 8 carbon atoms in the heteroaryl radical and at least one heteroatom selected from N, O and S which can be substituted with at least one group selected from $C_1$-$C_6$-alkyl groups and/or halogen atoms;

aryl-, aryl-$C_1$-$C_6$-alkyl groups with 5 to 12 carbon atoms in the aryl radical which if necessary can be substituted with at least one $C_1$-$C_6$-alkyl group and/or one halogen atom.

3. The method according to claim 1, characterized in that in addition to the ionic liquid, the reaction medium also contains a further solvent.

4. The method according to claim 1, characterized in that the further solvent is water or an organic solvent.

5. The method according to claim 1, characterised in that the reaction is carried out at temperatures of −10° C. to 130° C.

6. The method according to claim 1, characterised in that the reaction is carried out in a single-phase fashion or in a multiphase reaction system.

7. A composition comprising a lipase and at least one ionic liquid, wherein the lipase is dissolved in or suspended in the ionic liquid.

8. A composition comprising a lipase and at least one ionic liquid, wherein the lipase is dissolved in or suspended in the ionic liquid, characterised in that the ionic liquid is defined as in claim 2.

9. The composition according to claim 7, characterised in that it additionally contains a substrate.

10. The composition according to claim 8, characterised in that it contains the ionic liquid as a reaction medium or as a constituent of the reaction medium.

* * * * *